United States Patent [19]

Oloff et al.

[11] 4,207,889
[45] Jun. 17, 1980

[54] INJECTION SYSTEM FOR SUSPENSION AND SOLUTIONS

[75] Inventors: Clarence M. Oloff; Willi J. Buehring, both of Dayton; Kevin J. Greenlees, Fairborn, all of Ohio

[73] Assignee: The United States of America as represented by the Secretary of the Air Force, Washington, D.C.

[21] Appl. No.: 955,296

[22] Filed: Oct. 27, 1978

[51] Int. Cl.² .............................................. A61J 7/00
[52] U.S. Cl. ............................. 128/213 R; 128/214 F; 128/DIG. 1
[58] Field of Search ........... 128/213 R, 214 R, 214 A, 128/214 F, 215, 216, 224, 230, 234, 218 A, DIG. 1, DIG. 12; 222/145

[56] References Cited

U.S. PATENT DOCUMENTS

| 2,254,994 | 9/1941 | Butland | 128/214 A |
| 2,954,028 | 9/1960 | Smith | 128/214 R |
| 3,941,126 | 3/1976 | Dietrich et al. | 128/214 R |

Primary Examiner—John D. Yasko
Attorney, Agent, or Firm—Joseph E. Rusz; Richard J. Killoren

[57] ABSTRACT

An injection system for suspensions and solutions having five cartridges supported on a cartridge support. The cartridges are connected to a coalescing disc with five inlet passages and a single output passage with a feed line connected to the single passage. Suspensions and solutions supplied to the cartridges are selectively injected into a test subject by supplying a saline solution to the cartridge from a syringe pump through a selector which selects the cartridge to which the saline solution is supplied.

4 Claims, 7 Drawing Figures

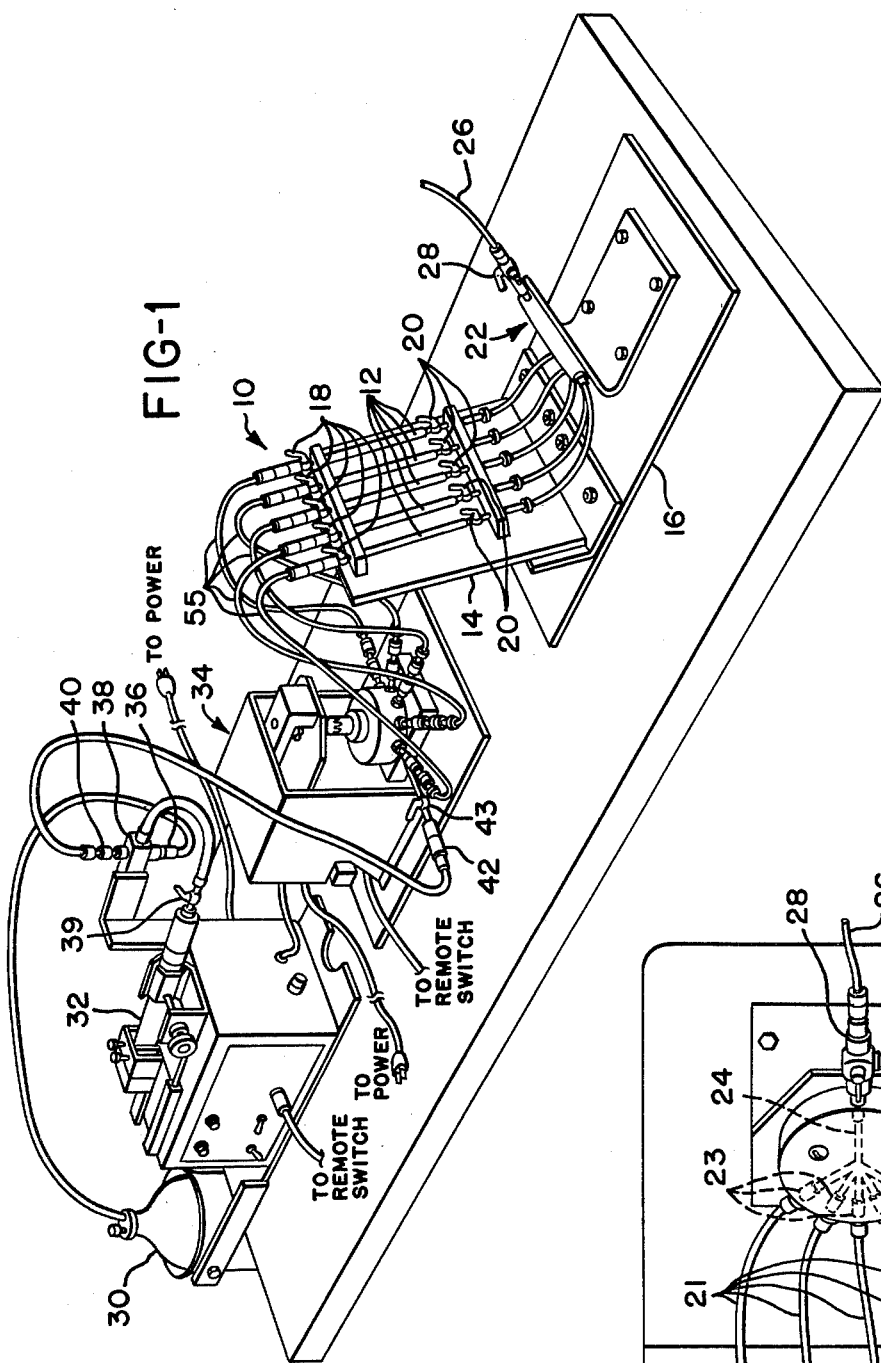
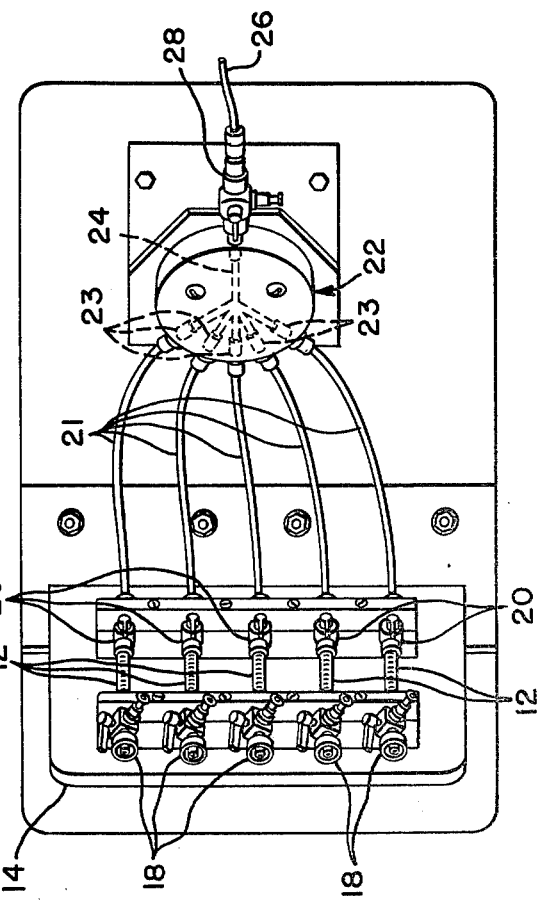

INJECTION SYSTEM FOR SUSPENSION AND SOLUTIONS

RIGHTS OF THE GOVERNMENT

The invention described herein may be manufactured and used by or for the Government of the United States for all governmental purposes without the payment of any royalty.

BACKGROUND OF THE INVENTION

This invention relates to a system for injecting various suspensions and solutions into test subjects.

In conducting various tests it is sometimes necessary to selectively inject different suspensions or solutions into a test animal. In some of these experiments it is necessary to remotely inject potentially hazardous materials, such as radioactive microspheres into test animals as in the determination of blood flow to various regions, organs or tissue and to measure cardiac output of animals exposed to gravitational forces in a centrifuge. In these experiments a system is needed to accomplish the multiple injections accurately and safely.

BRIEF SUMMARY OF THE INVENTION

According to this invention measured amounts of the different suspensions or solutions that are to be selectively injected into a test subject are located in a plurality of cartridges on a support. The cartridges are connected to a coalescing disc with an output line connected to the test subject. A syringe pump is provided to supply a measured amount of carrier solution to the cartridges through a sequencing device. One way valves are provided in the line between the solution reservoir and a three way connector and between the three way connector and the sequencing device. The syringe pump is connected to the third port of the three way connector.

IN THE DRAWINGS

FIG. 1 is a partially schematic isometric view of the injection system according to the invention.

FIG. 2 is a top view of the cartridge support system and the coalescing device for the device of FIG. 1.

DETAILED DESCRIPTION OF THE INVENTION

Figure 3:
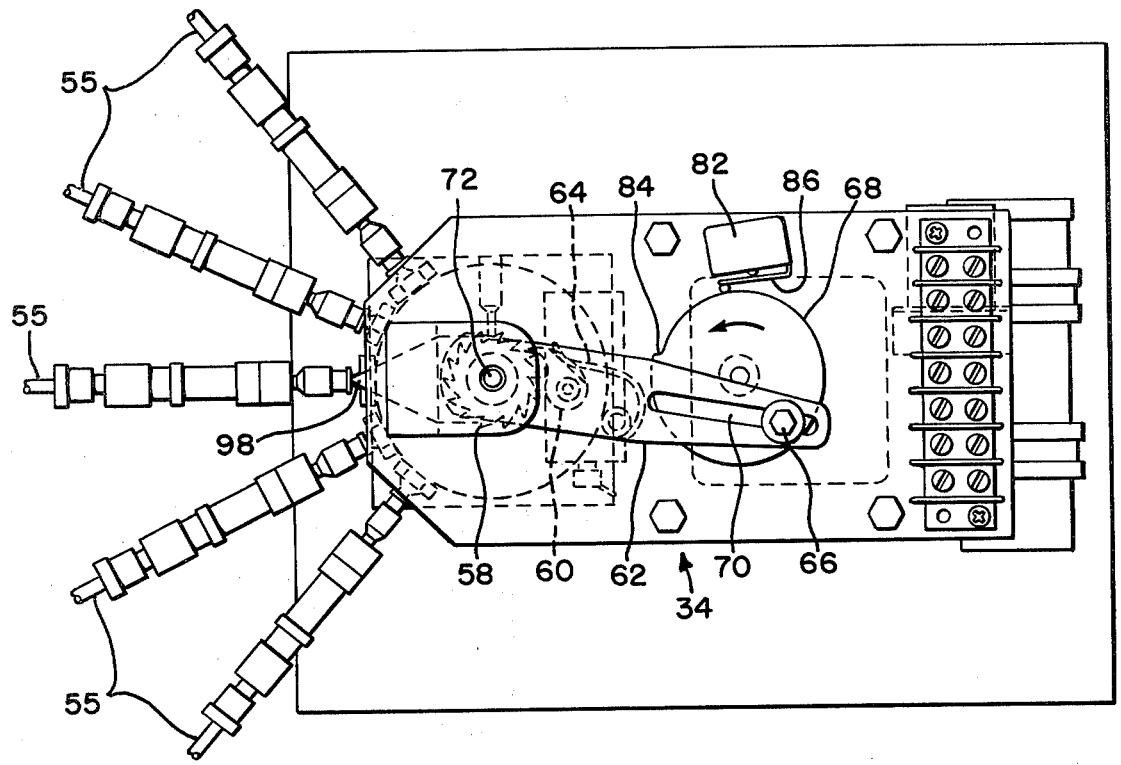
FIG. 3 is a top view of the sequencer for the device of FIG. 1, with the protective cover removed.

Reference is now made to FIG. 1 of the drawing which shows an injection system 10 for selectively injecting measured amounts of different suspensions or solutions into a test subject, such as an animal on a centrifuge.

The injection system includes a plurality of cartridges 12, with graduation markings, on a support member 14. In the device constructed the cartridges were 1 cc syringe barrels. The support member is secured to a plate member 16. A plurality of one way stopcocks 20 are connected to the lower ends of cartridges 12. The stopcocks 20 are connected to a plurality of flexible tubes 21 leading to a coalescing disc 22.

The coalescing disc has five input passages 23, connected to tubes 21, and a single output passage 24, connected to a supply line 26, leading to the test subject. A three way stopcock 28 is connected in the supply line 26 adjacent output 24.

A solution, such as heparinized saline solution, is selectively supplied to the cartridges 12, from a reservoir 30, by means of a syringe pump 32 and a sequencer 34.

The syringe pump 32 is a conventional syringe pump used to provide a measured amount of solution to the cartridges 12. In the device constructed the syringe pump was a model 197 automatic injector Sage pump.

The reservoir 30 is connected to the syringe pump 32 through a one way valve 36 and a three way connector 38. The syringe pump 32 is connected to the sequencer 34 through a three way stopcock 39, the three way connector 38, two one way valves 40 and 42 and a three way stopcock 43. The one way valves 36 and 40 permit the syringe pump 32 to draw solution from reservoir 30 and to supply solution to the sequencer 34. The one way valve 42 prevents any reverse flow in the line between the sequencer 34 and the syringe pump 32.

Figure 5:
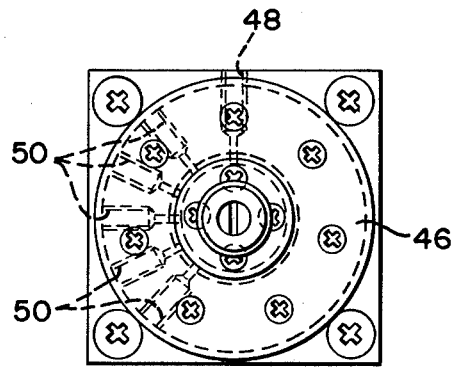
FIG. 5 is a top view of the sequencing selector for the device of FIG. 3.
Figure 6:
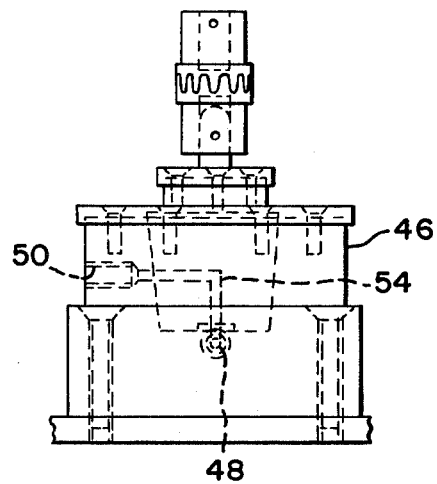
FIG. 6 is a partially schematic side elevation of the device of FIG. 5 corrsponding to the view shown in FIG. 4.

The sequencer 34 includes a selector manifold 46 having an inlet passage 48 and five output passages 50, shown in FIG. 5. A sequencer cylinder 52 fits into the selector manifold 46 and has a passage 54 for selectively connecting inlet passage 48 to one of the five output passages 50, as shown in FIG. 6.

Figure 4:
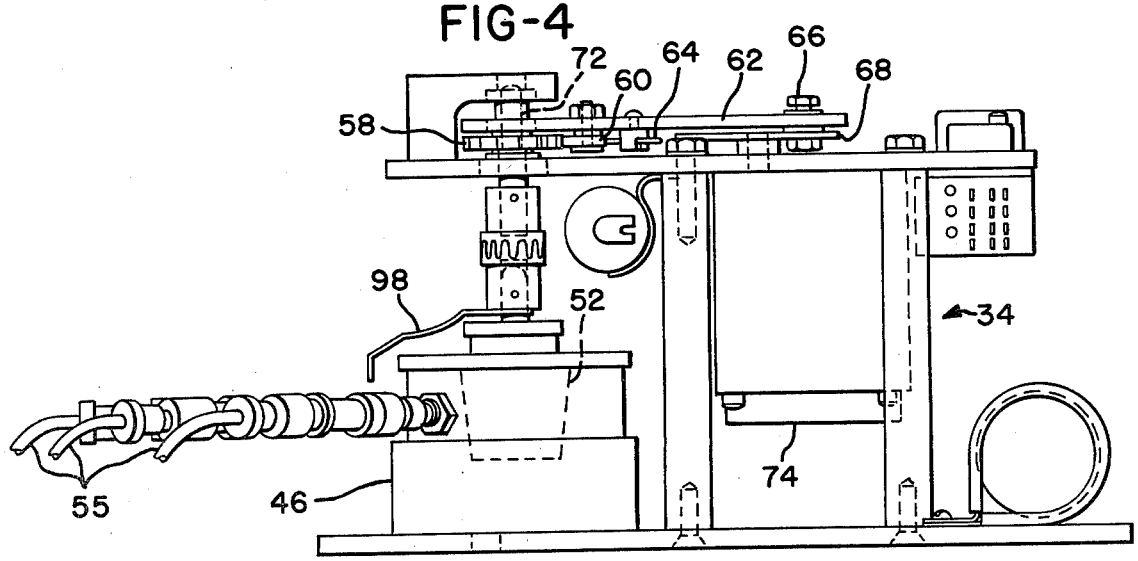
FIG. 4 is a side elevation of the device of FIG. 3 as viewed from the reverse side of that shown in FIG. 1.
Figure 7:
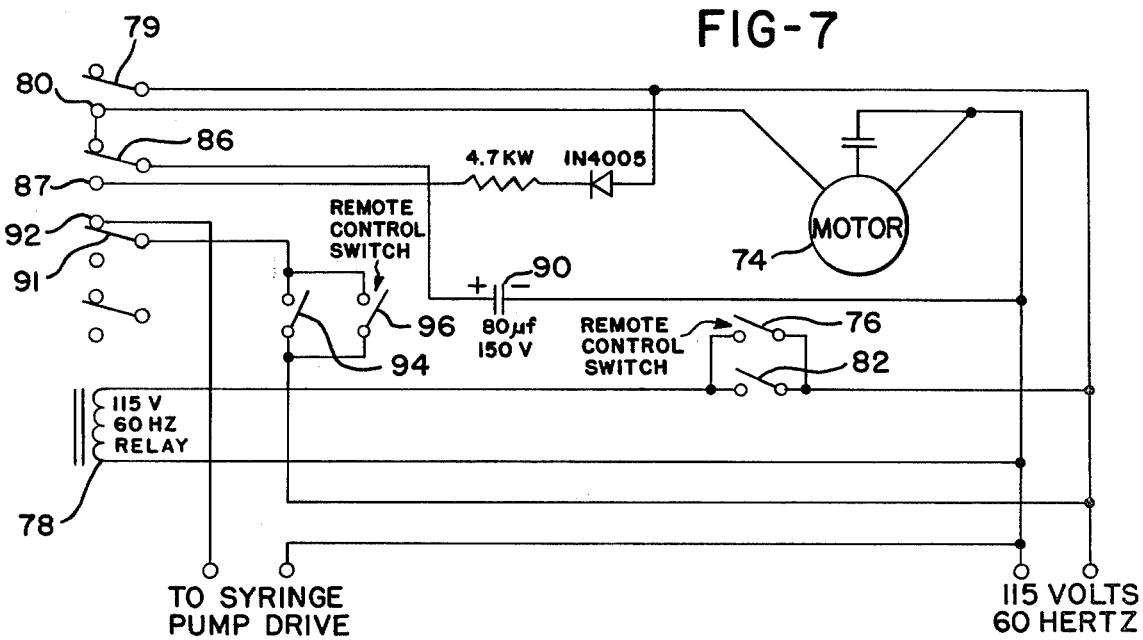
FIG. 7 is a circuit schematic for the injector system shown in FIG. 1.

The sequencer cylinder 52 is stepped from one passage 50 to the next by a ratchet wheel 58 driven by a pawl 60, shown in FIGS. 3 and 4. The pawl 60 is secured to a guide plate 62 and is held in engagement with the ratchet wheel 58 by a spring 64. A bolt 66 is secured to a cam wheel 68 and slides in slot 70 in guide plate 62 as the cam wheel rotates. This causes the guide plate to rotate around shaft 72 as the cam wheel rotates. As the guide plate rotates it moves the pawl against the ratchet wheel 58 to step the passage 54 from one passage 50 to the next for each rotation of cam wheel 68. The cam wheel 68 is driven by a motor 74 which is controlled as will be described with reference to FIG. 7.

A remote control switch 76 is operated to close the circuit through relay 78. This closes contacts 79 and 80 to supply power to the motor 74. As the motor starts to rotate cam wheel 68 closes the contacts of microswitch 82 which maintains the energization of relay 78 when switch 76 is opened. The switch 82, after closing, is held closed for the remainder of one revolution of motor 74 by cam 68. When the cam step 84 passes the microswitch operating arm 86, the switch 82 is opened to stop the motor.

When relay 78 is energized, in addition to starting motor 74, it also closes contacts 86 and 87 to close the charging circuit for braking capacitor 90 and opens contacts 91 and 92 to prevent the operation of the syringe pump during the stepping operation of the sequencer 34. The syringe pump can be operated either by closing switch 94 or by closing remote control switch 96.

In the operation of the device the five three way stopcocks 18 and five one way stopcocks 20 are opened. A solution such as heparinized saline solution is supplied through three way stopcock 28 to fill the coalescing disc, lines and cartridges 12 to the zero mark of each cartridge. The five valves 20 are then closed and the five cartridges are filled with the desired microspheres suspension or other solution. This can be accomplished with the use of a loading device as described in our copending application "Microsphere Loading Device", Serial No. 929,469 filed July 31, 1978.

The three way stopcocks 18 are then closed and stopcocks 20 are opened. The lines from the sequencer are then connected to the stopcocks 18. After filling all the lines and bleeding all the air from the system with the use of three way stopcocks 18, 28, 39 and 43, the supply line 26 can be connected to the test subject in a conventional manner. All the stopcocks are then opened to permit flow through the system.

The sequencer switch 76 is then operated to position the passage 54 in line with the first passage 50 in the sequencer. A marker 98 indicates the position of the sequencer. Switch 96 can then be operated to supply a measured amount of heparinized saline solution to the first cartridge to carry the microsphere suspension or solution in the first cartridge to the test animal. The sequencer is again operated to step the passage 54 to the second passage 50 with the above procedure being repeated until as many suspensions or solutions, up to five for the device constructed, have been injected into the test subject. A suspension or solution in any cartridge can be skipped by operating the selector without operating the pump.

In the device constructed the ratchet wheel had 14 steps so that nine operations of the switch 76 are required to return the passage 54 to the first passage 50 after a complete cycle for the cartridges has been made.

There is thus provided an apparatus for injecting various suspensions and solutions into test subjects.

We claim:

1. An apparatus for injecting suspensions and solutions into a test subject supply line, comprising: a cartridge support member; a plurality of cartridges secured to said support member; a coalescing disc having a single outlet passage connected to a plurality of inlet passages; means for connecting said test subject supply line to the single outlet passage of the coalescing disc; means for connecting each of said cartridges to one inlet of said coalescing disc; means for selectively supplying a measured amount of carrier solution sequentially to said cartridges to carry the suspension and solutions therein through the coalescing disc into the test subject supply line; said means for supplying carrier solution sequentially to the cartridges includes a sequencer having a cylinder block with one inlet passage and a plurality of outlet passages; means for connecting said outlet passages to said cartridges; means for sequentially connecting said inlet passage to said outlet passages and means for supplying measured amounts of solution to said inlet passage; said means for sequentially connecting said inlet passage to said outlet passages including a cylinder positioned within said cylinder block; said cylinder including a passage adapted to sequentially connect said inlet passage to said outlet passages; means for stepping the passage within said cylinder sequentially into alignment with said outlet passages.

2. The device as recited in claim 1 wherein said means for sequentially stepping the passage within the cylinder into alignment with the outlet passages includes a rachet wheel connected to said cylinder; an electric motor; means, connected to said electric motor for stepping said rachet wheel to move the passage within said cylinder from one outlet passage to the next for each revolution of said motor; means for stopping said motor after each revolution.

3. The device as recited in claim 2 wherein said means for stopping said motor after each revolution includes a cam wheel connected to said electric motor; a microswitch positioned adjacent said cam wheel; means for energizing said electric motor; said means for energizing said electric motor including a power supply; a relay, including switch contacts connected between said power supply and said motor; means, connected in parallel with said microswitch for energizing said relay to start said motor; said cam including means for closing the microswitch contacts for maintaining the energization of the motor for one revolution of the motor.

4. The device as recited in claim 3 wherein said means for supplying measured amounts of solution to the inlet passage of the cylinder block includes a syringe pump; a three way connector having a first port connected to the syringe pump; a solution supply; said three way connector having a second port connected to the solution supply; means, connected between the solution supply and the three way connector, for permitting only one way flow from the solution supply to the syringe pump; said three way connector having a third port connected to the inlet passage in said cylinder block; means, connected between the three way connector and said cylinder block inlet passage for permitting only one way flow from the syringe pump to the cylinder block inlet passage.

* * * * *